(12) United States Patent
Bolli et al.

(10) Patent No.: US 8,324,232 B2
(45) Date of Patent: Dec. 4, 2012

(54) 4-PYRIMIDINESULFAMIDE DERIVATIVE

(75) Inventors: Martin Bolli, Allschwil (CH);
Christoph Boss, Allschwil (CH);
Alexander Treiber, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 402 days.

(21) Appl. No.: 12/673,413

(22) PCT Filed: Aug. 15, 2008

(86) PCT No.: PCT/IB2008/053282
§ 371 (c)(1),
(2), (4) Date: Feb. 12, 2010

(87) PCT Pub. No.: WO2009/024906
PCT Pub. Date: Feb. 26, 2009

(65) Prior Publication Data
US 2012/0142716 A1 Jun. 7, 2012

(30) Foreign Application Priority Data

Aug. 17, 2007 (WO) .................. PCT/IB2007/053292
Jun. 26, 2008 (WO) .................. PCT/IB2008/052571

(51) Int. Cl.
*A01N 43/54* (2006.01)
*A61K 31/505* (2006.01)

(52) U.S. Cl. ........................ 514/274; 544/296
(58) Field of Classification Search .................. 544/296; 514/274
See application file for complete search history.

(56) References Cited

U.S. PATENT DOCUMENTS

| | | | |
|---|---|---|---|
| 4,233,294 A | 11/1980 | Maurer et al. | |
| 5,292,740 A | 3/1994 | Burri et al. | |
| 7,094,781 B2 | 8/2006 | Bolli et al. | |
| 7,285,549 B2 | 10/2007 | Bolli et al. | |
| 7,976,869 B2 | 7/2011 | Blouquin et al. | |
| 2001/0056183 A1 | 12/2001 | Wu et al. | |
| 2002/0076436 A1 | 6/2002 | Batra et al. | |
| 2004/0062803 A1 | 4/2004 | Hedden et al. | |
| 2004/0077670 A1 | 4/2004 | Bolli et al. | |
| 2008/0233188 A1 | 9/2008 | Adesuyi et al. | |
| 2009/0318459 A1 | 12/2009 | Clozel | |
| 2010/0004274 A1 | 1/2010 | Adesuyi et al. | |
| 2010/0311774 A1 | 12/2010 | Clozel et al. | |
| 2011/0136818 A1 | 6/2011 | Clozel | |

FOREIGN PATENT DOCUMENTS

| | | |
|---|---|---|
| EP | 0 526 708 | 2/1993 |
| EP | 0 633 259 | 1/1995 |
| EP | 0 657 548 | 6/1995 |
| EP | 0 743 307 | 11/1996 |
| EP | 0 747 050 | 12/1996 |
| EP | 0 882 719 | 12/1998 |
| EP | 0 959 072 | 11/1999 |
| JP | 2001-335469 | 12/2001 |
| JP | 4-103525 A | 1/2002 |
| WO | WO 96/16963 | 6/1996 |
| WO | WO 96/19459 | 6/1996 |
| WO | WO 00/42035 | 7/2000 |
| WO | WO 01/17976 | 3/2001 |
| WO | WO 01/46156 | 6/2001 |
| WO | WO 01/81335 | 11/2001 |
| WO | WO 01/81338 | 11/2001 |
| WO | WO 02/00216 | 1/2002 |
| WO | WO 02/46172 | 6/2002 |
| WO | WO 02/053557 | 7/2002 |
| WO | WO 2002/053557 | 7/2002 |
| WO | WO 02053557 A1 * | 7/2002 |
| WO | WO 03/043602 | 5/2003 |
| WO | WO 03/072139 | 9/2003 |
| WO | WO 2004/075894 | 9/2004 |
| WO | WO 2007/031933 | 3/2007 |

OTHER PUBLICATIONS

R. Benza et al., 63 Journal of Heart and Lung Transplantation, 63-69 (2007).*
E. Gabbay et al., 36 Vascular Health and Risk Management, 887-900 (2007).*
Lee, J., et al., 2-Benzyl and 2-Phenyl-3-Hydroxypropyl Pivalates as Protein Kinase C Ligands, Bioorganic and Medicinal Chemistry, vol. 14, pp. 2022-2031, (2006).
Breu, V., et al., in Vitro Characerization of Ro 46-2005, A Novel Synthetic Non-Peptide Endothelin Antagonist of $ET_A$ and $ET_B$ Receptors, Federation of European Biochemical Societies (FEBS), vol. 334, No. 2, pp. 210-214, (1993).
Dewynter, G., et al., Synthèse de "Sulphydantöines" Chirales. Aspects Stéréochimiques et Protection Régiospécifique., Tetrahedron, vol. 49, No. 1, pp. 65-76, (1993).
Gomtsyan, A., et al., Design, Synthesis and Structure-Activity Relationship of 6-Alkynylpyrimidines as Potent Adenosine Kinase Inhibitors, J. med. Chem. vol. 45, pp. 3639-3648, (2002).

(Continued)

*Primary Examiner* — James O Wilson
*Assistant Examiner* — Alexander R Pagano
(74) *Attorney, Agent, or Firm* — Hoxie & Associates LLC

(57) ABSTRACT

The invention relates to the compound of structural formula (I) and the salts thereof. Said compound is useful as endothelin receptor antagonist. The invention further relates to a process for preparing said compound.

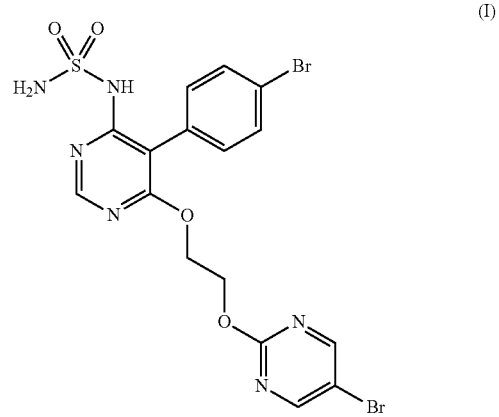

(I)

8 Claims, No Drawings

OTHER PUBLICATIONS

Gould, P.L.., Salt Selection for Basic Drugs, Int. J. Pharm., vol. 33, pp. 201-217, (1986).
Olson, R.E., et al., Orally Active Isoxazolline Glycoprotein IIb/IIIa Antagonists with Extended Duration of Action, J. Med. Chem., vol. 42, pp. 1178-1192, (1999).
Neidhart, W., et al., The Discovery of Nonpeptide Endothelin Receptor Antagonists. Progression towards Bosentan, Chimia, vol. 50, pp. 519-524, (1996).
Winum, J.-Y., et al., N-(tert-Butoxycarbonyl)-N[4-(dimethylazaniumylidene)-1,4-dihydropyridin-1-ylsulfonyl]azanide:A New Sulfamoylating Agent. Structure and Reactivity toward Amines, Organic Letters, vol. 3, No. 14, pp. 2241-2243, (2001).
Remington, The Science and Practice of Pharmacy, $21^{st}$ Edition, Part 5, "Pharmaceutical Manufacturing", [published by Lippincott Williams and Wilkins] (2005).
Ghassemi, S., et al., Alternative method of Boc-removal from sulfamide using silica-phenyl sulfonic acid in conjunction with microwave heating, Molecular Diversity, vol. 9, pp. 295-299, (2005).
Handbook of Pharmaceutical Excipients, Third Edition, Edited by Arthur H. Kibbe, American Pharmaceutical Association, Washington, D.C., USA and Pharmaceutical Press, London, UK (2000).
"Lexikon der Hilfsstoffe fur Pharmazie, Kosmetik and Angrenzende Gebiete" edited by H.P. Fiedler, Fourth Edition, Edito Cantor, Aulendorf (1996).
Hagers Handbuch der Pharmazeutischen Praxis, Fourth Edition, (1971), Springer Verlag, Berlin, Heidelberg, New York.
Hagers Handbuch der Pharmazeutischen Praxis, Fourth Edition, (1977), Springer Verlag, Berlin, Heidelberg, New York.
Remington's Pharmaceutical Sciences, $13^{th}$ Edition, Mach Publishing Company, (1975), Easton, PA, USA.
ROMPP Online 2007, George Thieme Verlag, Stuttgart, DE.
Arai, et al. Cloning and Expression of a cDNA Encoding an Endothelin Receptor Nature, 348:730-732, (1990).
Banker, G., et al., "Modern Pharmaceutics", Chapters 10 & 11, $4^{th}$ Edition, vol. 121, pp. 447-451, 458, 464-465, 469, 471, 548 and 550 (2006).
Bennett, J. Claude, et al., Textbook at Medicine, vol. 1, $20^{th}$ Edition 1004-1010, (1996).
Cohen, E., et al., Sulfamoyl Chloride, Sulfamides and Sulfimide, J. Am. Chem., vol. 84, pp. 1994-2002 (1962).
Crosby, D., et al., n-Butyl 5-Chloro-2-Pyrimidoxyacetate-A Plant Growth Regulator Analog. J. Org. Chem., vol. 25, pp. 1916-1919, (Nov. 1960).
Cujesov, V.I., et al., "Industrial Technology of Medicaments", Charkov, Publ., NFAU, MTK-Book, vol. 2, pp. 330-334, (2002).
Dewynter, et al., Tetrahedron, vol. 49, No. 1, pp. 65-76, (1993).
Dickinson, R. et al., Thromboxane Modulating Agents. 3. iH-Imidazol-1-ylalkyl-and 3-Pyridinylalkyl-Substituted 2[1-(Arylsulfonyl)amino]ethyl]benzenepropanoic Acid Derivatives as Duel Thromboxane Synthase Inhibitor/Thromboxane Receptor Antagonists, J. Med. Chem., vol. 40, pp. 3442-3452 (1997).
Gohring, W., et al., Development of a Process to Prepare 2-Cyanaopyrimidine on Commercial Scale, Chimia, vol. 50, (Nov. 1996).
Graf, R., Chem. Bar. vol. 92, pp. 509-513, (1959).
Kloek, J., et al., "An Improved Synthesis of Sulfamoyl Chlorides", J. Org. Chem. 4028, (1976).
Kohara, Y., et al., Synthesis and Angiotensin II Receptor Antagonistic Activities at Benzimidazote Derivatives Bearing Acidic Heterocycles as Novel Tetrazole Biososteres, J. Med. Chem., vol. 39, pp. 5228-5235, (1996).
Lachman, et al., "The Theory and Practice of Industrial Pharmacy", Third Edition, (1986) Lea & Febeger, Philadelphia, PA USA.
Lieberman, et al., Pharmaceutical Dosage Forms: Tablets vol. 1, $2^{nd}$ Edition, Revised and Expanded, (1990).
McMillen, M., et al., "Endothelins: Polyfunctional Cytokines", J. Amer. College of Surgeons, vol. 180, pp. 621-640, (1995).
March, Jerry, Advance Organic Chemistry, Fourth Edition, p. 499 end references cited therein (1992).
Morgan, E.D., Synthesis of p-Alkylphenylacetic Acids, Tetrahedron, vol. 23, pp. 1735-1738, (1967).
Neidhart, W., et al., Discovery of R048-5695: A Potent Mixed Endothelin Receptor Antagonist Optimized from Bosentan, Bioorganic & Medical Chemistry Letters, vol. 7, No. 17, pp. 2223-2228, (1997).
Nugent, A., et al., Pyrimidine Thioethers: A Novel Class of HIV Reverse Transcriptase Inhibitors with Activity Against BHAP-Resistant HIV, J. Med. Chem., vol. 41, pp. 3793-3803, (1998).
Ogawa, V. et al., Molecular Cloning of a Non-Isopeptide-Selective Human Endothelin Receptor, Biochem. Biophy. Research Comm. vol. 178(1)pp. 248-255, (Jul. 1991).
Ohlstein, E., et al., Endothelin-1-Modulates Vascular Smooth Muscle Structure and Vasomotion: Implications in Cardiovascular Pathology, Drug Development Research, vol. 29, pp. 108-128, (1993).
Remington, The Science and Practice of Pharmacy, $21^{st}$ Edition, Part 5, "Pharmaceutical Manufacturing", pp. 720-744 (Ch. 38) (2005).
Remington, The Science and Practice of Pharmacy, $21^{st}$ Edition, Part 5, "Pharmaceutical Manufacturing", pp. 802-805 (Ch. 41) (2005).
Remington, The Science and Practice of Pharmacy, $21^{st}$ Edition, Part 5, "Pharmaceutical Manufacturing", pp. 889-894 (Ch. 45) (2005).
Rubanyi, G.M., et al., "Endothelins: Molecular Biology, Biochemistry, Pharmacology, Physiology and Pathophysiology," Pharm. Reviews, vol. 46, No. 3 (1994).
Sakurai, et al., "Cloning of a cDNA Encoding a Non-Isopeptide-Selective Subtype at the Endothelin Receptor", Nature, vol. 348, pp. 732-735, (Dec. 1990).
Simone, Oncology: Introduction, Cecil Textbook of Medicine, 20th Edition, vol. 1, pp. 1004-1010, (1996).
SPH USSR 11 publ., ed. 2., "Common Methods of Analyzing Medicinal Plant Materials—Moscow", Medicina, p. 159 [D3], (1990).
Sucker, et al., "Pharmazeutische Tehnologies", (1991), Georg Thieme Verlag Stuttgart—New York.
Sumner, T. et al., "Endothelin Eta and ETb Receptors Mediate Vascular Smooth Muscle Contraction", Br. J. Pharmacol., vol. 107, pp. 858-860, (1992).
Tozer, M., et al., 4-Chlorbenzyl Sulfonamide and Sulfamide Derivatives of Histamine Homologues: The Design of Potent Histamine H3 Receptor Antagonists Bioorganic & Medicinal Chemistry Letters, vol. 9, pp. 3103-3106, (1999).
Weiss, G., et al., Liebigs Ann. Chem. vol. 729, pp. 40-51, (1969).
Yanagisawa, M., et al., "A Novel Potent Vasoconstrictor Peptide Produced by Vascular Endothelial Cells", Nature, vol. 332, pp. 411-415, (Mar. 1988).

\* cited by examiner

4-PYRIMIDINESULFAMIDE DERIVATIVE

CROSS REFERENCE TO RELATED APPLICATIONS

This application is a United States Application under 35 U.S.C. 371 claiming benefit of PCT Application No. PCT/IB2008/053282, filed on Aug. 15, 2008, which claims the benefit of PCT Application No. PCT/IB2007/053292, filed on Aug. 17, 2007 and PCT Application No. PCT/IB2008/052571, filed on Jun. 26, 2008.

The present invention concerns {5-(4-bromo-phenyl)-6-[2-(5-bromo-pyrimidin-2-yloxy)-ethoxy]-pyrimidin-4-yl}-sulfamide and the salts thereof, a process for preparing that compound and the use thereof in medicine.

{5-(4-bromo-phenyl)-6-[2-(5-bromo-pyrimidin-2-yloxy)-ethoxy]-pyrimidin-4-yl}-sulfamide has the formula I

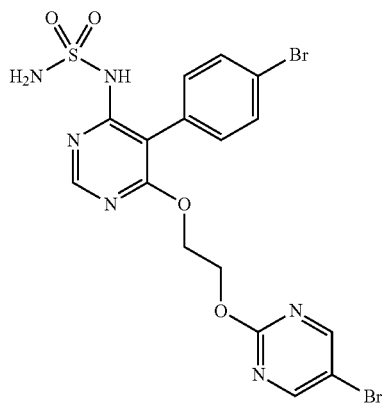

The compound of formula I is an endothelin receptor inhibitor and useful as endothelin receptor antagonist. The compound of formula I is a new member of a structural family that was previously generically disclosed in WO 02/053557.

The Applicant has now surprisingly found that the compound of formula I possesses improved properties when compared to structurally close compounds that were specifically disclosed in WO 02/053557. In particular, the compound of formula I, while showing endothelin receptor antagonist activity, exhibits in vivo a much longer half-life and a much shorter clearance in comparison to corresponding alkylated derivatives. This makes the compound of formula I particularly suitable for long-acting pharmaceutical compositions.

Because of its ability to inhibit the endothelin binding, the compound of formula I can be used for treatment of diseases which are associated with an increase in vasoconstriction, proliferation or inflammation due to endothelin. Examples of such diseases are hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome, digital ulcers and portal hypertension. They can also be used in the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, therapy and prophylaxis of diabetic complications, complications of vascular or cardiac surgery or after organ transplantation, complications of cyclosporin treatment, pain, hyperlipidemia as well as other diseases, presently known to be related to endothelin.

The compound of formula I and its pharmaceutically acceptable salts can thus be used as medicaments, e.g. in the form of pharmaceutical compositions for enteral or parental administration.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The invention therefore firstly relates to the compound of formula I or a salt (in particular a pharmaceutically acceptable salt) thereof.

The invention also relates to the compound of formula I or a pharmaceutically acceptable salt thereof as a medicament.

The invention further relates to pharmaceutical compositions containing, as active principle, the compound of formula I or a pharmaceutically acceptable salt thereof, and at least one therapeutically inert excipient.

Besides, the compound of formula I and its pharmaceutically acceptable salts may be used for the preparation of a medicament, and are suitable for the treatment of hypertension, pulmonary hypertension (especially pulmonary arterial hypertension), coronary diseases, cardiac insufficiency, renal and myocardial ischemia, renal failure, cerebral ischemia, dementia, migraine, subarachnoidal hemorrhage, Raynaud's syndrome, digital ulcers or portal hypertension as well as for the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, diabetic complications, complications of vascular or cardiac surgery or after organ transplantation, complications of cyclosporin treatment, pain or hyperlipidemia.

More particularly, the compound of formula I and its pharmaceutically acceptable salts may be used for the preparation of a medicament, and are suitable for the treatment of a disease selected from the group consisting of hypertension, pulmonary hypertension (including pulmonary arterial hypertension), diabetic artcriopathy, heart failure, erectile dysfunction and angina pectoris.

According to a particularly preferred variant of the invention, the compound of formula I and its pharmaceutically acceptable salts may be used for the preparation of a medicament, and are suitable for the treatment of hypertension (notably arterial hypertension).

According to another particularly preferred variant of the invention, the compound of formula I and its pharmaceutically acceptable salts may be used for the preparation of a medicament, and are suitable for the treatment of pulmonary hypertension (especially pulmonary arterial hypertension).

The compound of formula I can be manufactured as explained in WO 02/053557 or as described later in the specification (notably in the Example).

The production of the pharmaceutical compositions can be effected in a manner which will be familiar to any person skilled in the art (see for example Remington, *The Science* and Practice of Pharmacy, 21st Edition (2005), Part 5, "Pharmaceutical Manufacturing" [published by Lippincott Williams & Wilkins]) by bringing the described compound of formula I or its pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compound of formula I can be manufactured in accordance with the present invention using the procedures described hereafter.

Preparation of the Compound of Formula I

Abbreviations:

The following abbreviations are used throughout the specification and the examples:

Ac acetyl aq. aqueous br. broad

Boc tert-butoxycarbonyl t-Bu tert-butyl

DAD diode array detector

DBU 1,8-diazabicyclo(5.4.0)undec-7-ene

DCM dichloromethane

DMAP 4-dimethylaminopyridine

DME 1,2-dimethoxyethane

DMF N,N-dimethylformamide

DMSO dimethylsulfoxide

EA ethyl acetate

ET endothelin ether diethyl ether

Hex hexane

HV high vacuum conditions

LC Liquid Chromatography

McOH methanol

MS Mass Spectroscopy

NMR nuclear magnetic resonance org. organic rt room temperature

TEA triethylamine

THF tetrahydrofuran

TLC thin layer chromatography $t_R$ retention time

General Preparation Methods:

The compound of formula I can be manufactured according to the general sequence of reactions outlined below, by the methods given in the Example or by analogous methods. Optimum reaction conditions may vary with the particular reactants or solvents used, but such conditions can be determined by a person skilled in the art by routine optimisation procedures. Only a few of the synthetic possibilities leading to the compound of formula I are described.

The compound of formula I thus obtained may, if desired, be converted into its salts, and notably into its pharmaceutically acceptable salts, by standard methods.

The compound of formula I can be obtained from a compound of formula I-1

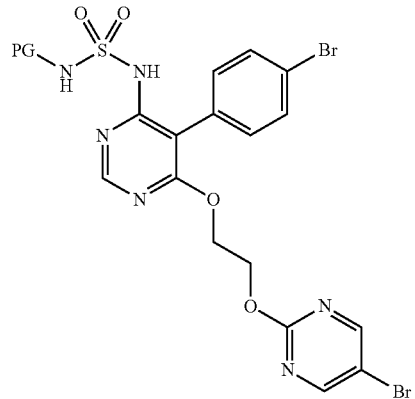

wherein PG represents a suitable protecting group, by cleaving the protecting group PG. Suitable protecting groups PG are, for instance, a benzyl group, which can be cleaved by e.g. $BCl_3$ or $BBr_3$ (for example in a solvent such as chloroform), or a 4-methoxy- or a 2,4-dimethoxybenzyl group, which can be cleaved oxidatively by e.g. cerium ammonium nitrate (for example in a solvent such as a mixture of acetonitrile and water) or 2,3-dichloro-5,6-dicyano-benzoquinone (for example in a solvent such as DCM, 1,2-dichloroethane, acetone or toluene, in the presence or absence of water).

The compounds of formula I-1 can be prepared by reacting a compound of formula I-2

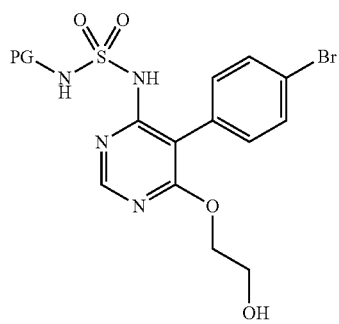

with a compound of formula I-3

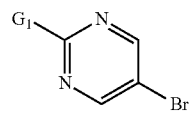

wherein $G_1$ represents a reactive group such as a chlorine or a bromine atom, or a methylsulfonyl or ethylsulfonyl group in the presence of a strong base such as LiH, NaH, $CaH_2$, etc. in a solvent such as THF, DMF, dioxane, etc. or mixtures thereof. Several compounds of formula I-3 are commercially available; the others can be prepared by the person skilled in the art by applying standard methodology.

The compounds of formula I-2 can be prepared by reacting a compound of formula I-4

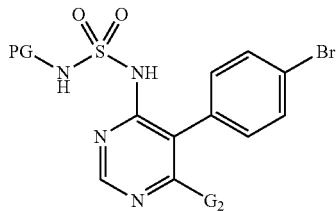

I-4 wherein G$_2$ represents a reactive group such as a halogen atom, preferably a chlorine, with ethylene glycol in the presence of a base such as potassium tert-butylate, NaH, LiH, etc. in the presence or absence of an additional solvent such as 1,2-dimethoxyethane, THF, dioxane (and notably in the presence of 1,2-dimethoxyethane), etc. preferably at elevated temperatures (e.g. between 50 and 100° C., in particular at temperatures from 80 to 100° C.).

The compounds of formula I-4 may be prepared by reacting a compound of formula I-5

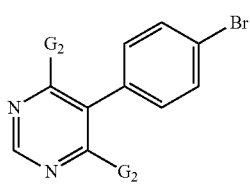

I-5 with a compound of formula I-6

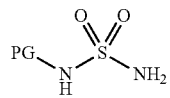

I-6 in the presence of a base such as potassium tert-butylate, TEA, ethyl-diisopropyl amine, etc., or, preferably, with a salt of a compound of formula I-6, preferably the potassium salt, in a solvent such as DMSO, DMF, THF, etc. or mixtures thereof in the presence or absence of an additional base at temperatures between 20 and 80° C., and preferably between 20 and 40° C.

The compounds of formula I-5 are prepared e.g. by treating the compound of formula I-7

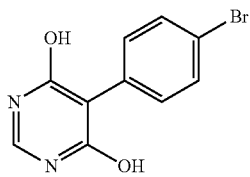

I-7 with POCl$_3$, PCl$_3$, PCl$_5$ or mixtures thereof, or POBr$_3$, in the presence or absence of tetraethylammonium chloride, triethylamine, or dimethyl- or diethylaniline, and in the presence or absence of an additional solvent such as chloroform, 1,2-dichloroethane, toluene, xylene, or acetonitrile at elevated temperatures (e.g. between 60 and 120° C.).

The compound of formula I-7 is prepared by reacting a compound of formula I-8

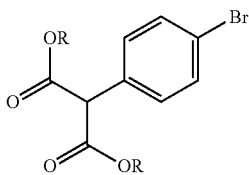

I-8 wherein R represents an alkyl group, and preferably a methyl or an ethyl group, with formamidine, or a salt thereof, in analogy to procedures given in the literature (e.g. A. Gomtsyan et al., *J. Med. Chem.* (2002), 45, 3639-3648; W. Neidhart et al., *Chimia* (1996), 50, 519-524).

The 2-(4-bromo-phenyl)-malonic acid ester of formula I-8 may be prepared from commercially available 4-bromophenylacetic acid in analogy to literature procedures (e.g. J. Lee, J.-H. Lee, S. Y. Kim, N. A. Perry, N. E. Lewin, J. A. Ayres, P. M. Blumberg, *Bioorg. Med. Chem.* 14 (2006), 2022-2031).

The sulfamides of formula I-6 may be prepared in a two step procedure from chlorosulfonyl isocyanate in analogy to literature procedures (e.g. G. Dewynter et al., *Tetrahedron* (1993), 49, 65-76; S. Ghassemi, K. Fuchs, *Molecular Diversity* (2005), 9, 295-299; J.-Y. Winum et al., *Organic Letters* (2001), 3, 2241-2243). In a first step, chlorosulfonyl isocyanate is reacted with tert-butanol and then, in a second step, with the appropriate amine PG-NH$_2$ to give the Boc-protected intermediate of a compound of formula I-6. In a third step, the Boc-group is cleaved under acidic conditions to give the compound of formula I-6. Alternatively, a compound of formula I-6 may be obtained in analogy to literature procedures (e.g. R. E. Olson, et al., *J. Med. Chem.* (1999), 42, 1178-1192, and literature cited therein) by reacting the appropriate sulfamoyl chloride intermediate of formula I-9

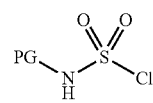

I-9 with ammonia.

Invention Process:

The invention therefore also relates to a process for the preparation of the compound of formula I as described above, which process comprises the following steps:

a) reacting a compound of formula I-2$_B$

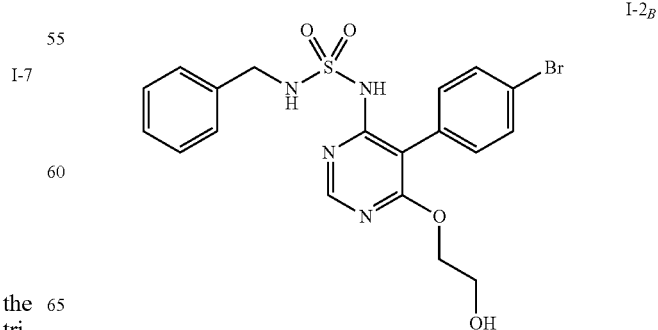

I-2$_B$ with a compound of formula I-3

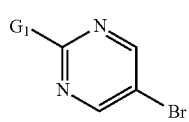

wherein G₁ represents a chlorine or bromine atom or a methylsulfonyl or ethylsulfonyl group (and in particular a chlorine atom), in the presence of a strong base; and
b) cleaving the benzyl group of the compound of formula I-1$_B$ obtained in step a)

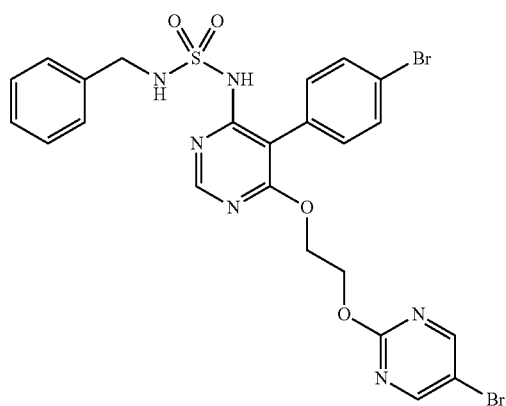

using BCl₃ or BBr₃.

Preferably, step a) of the above process will be carried out in a solvent selected from the group consisting of THF, DMF and dioxane, or a mixture of solvents selected from the group consisting of THF, DMF and dioxane (for example in a mixture of THF and DMF).

The strong bast of step a) of the above process will preferably be selected from the group consisting of LiH, NaH and CaH₂. For step a), the reaction will preferably take place at temperatures from 20° C. to the boiling temperature of the solvent, and in particular at temperatures between 20° C. and 70° C.

Preferably, step b) of the above process will be carried out in a solvent selected from the group consisting of chloroform and DCM, or in a mixture of chloroform and DCM (for example in chloroform), preferably at temperatures from 20° C. to 40° C., and in particular at temperatures from 20° C. to 30° C.

According to a preferred variant of the above process, the compound of formula I-2$_B$ will be prepared from a compound of formula I-4 as defined in the section "General preparation methods" (PG being benzyl) thanks to an additional step as described in the same section. Preferably, according to said variant, the compound of formula I-4 itself will be prepared from a compound of formula I-5 and a compound of formula I-6 (wherein PG is benzyl) as both defined in the section "General preparation methods" thanks to an additional step as described in the same section (which compound of formula I-5 and compound of formula I-6 can themselves be prepared thanks to additional steps as described in the section "General preparation methods").

The above process may also be directed to the preparation of a salt (in particular a pharmaceutically acceptable salt) of the compound of formula I. In this case, the process comprises the additional step of converting the compound of formula I obtained in step b) into its salt (in particular into its pharmaceutically acceptable salt).

Particular embodiments of the invention are described in the following Example, which serves to illustrate the invention in more detail without limiting its scope in any way.

EXAMPLE

The following example was prepared according to the procedures described below. All compounds were characterized by ¹H-NMR (300 MHz) and occasionally by ¹³C-NMR (75 MHz) (Varian Oxford, 300 MHz; chemical shifts are given in ppm relative to the solvent used; multiplicities: s=singlet, d=doublet, t=triplet; m=multiplet), by LC-MS (Finnigan Navigator with HP 1100 Binary Pump and DAD, column: 4.6×50 mm, Develosil RP Aqueous, 5 μm, 120 A, gradient: 5-95% acetonitrile in water, 1 min, with 0.04% trifluoroacetic acid, flow: 4.5 ml/min), $t_R$ is given in min; by TLC (TLC-plates from Merck, Silica gel 60 F₂₅₄) and occasionally by melting point.

Preparation A: Benzylsulfamide Potassium Salt

A.i. Benzylsulfamide

Chlorosulfonylisocyanate (14.14 g) was dissolved in DCM (50 mL) and cooled to 0° C. A solution of t-BuOH (9.6 mL) in DCM (50 mL) was added within 30 min. Stirring was continued for additional 30 min at rt. The solution thus obtained was then added at 0° C. within 1 h to a solution of benzylamine (10.7 g) and TEA (15.32 mL) in DCM (200 mL). Stirring is continued for 10 h at rt. The mixture was concentrated in vacuo, taken up in EA (500 mL) and washed with water (2×40 mL) and brine (30 mL), dried over MgSO₄, filtered. The filtrate was concentrated in vacuo and the crude material was crystallized from EA and dried under HV to give N-benzyl-N'-tert-butoxycarbonyl sulfamide (13.68 g).

¹H NMR (CDCl₃): δ 1.46 (s, 9H); 4.25 (s, 2H); 5.42 (s br., 1H); 7.30-7.40 (m, 5H).

LC-MS: $t_R$=0.90 min, [M+H]⁺=287.09.

This material was dissolved in dioxane (20 ml) and 4 M HCl in dioxane (120 mL) was added within 1 h at rt. The mixture was stirred for 8 h before the solvent was evaporated and the residue dried under HV to give benzylsulfamide as an off-white powder (9.47 g).

¹H NMR (D₆-DMSO): δ 4.05 (d, J=6.4 Hz, 2H); 6.60 (s, 2H); 7.04 (s, J=6.4 Hz, 1H); 7.20-7.36 (m, 5H).

LC-MS: $t_R$=0.60 min, [M+H+CH₃CN]⁺=228.17.

A.ii. Benzylsulfamide Potassium Salt

To a solution of benzylsulfamide (17.98 g) in McOH (300 mL) was carefully added potassium tert-butylate (10.8 g). The mixture was stirred at rt for 15 min before the solvent was evaporated. The remaining residue was dried under HV to give benzylsulfamide potassium salt as an off-white powder (21.73 g).

Preparation B:
5-(4-bromo-phenyl)-4,6-dichloro-pyrimidine

B.i. 4-bromophenylacetic acid methyl ester

To a solution of 4-bromophenylacetic acid (50 g) in methanol (250 ml) was added dropwise thionyl chloride (34.2 mL)

while the temperature of the reaction mixture was kept at 0-5° C. Upon complete addition cooling was stopped and the mixture was allowed to warm to rt. Stirring was continued for 75 min before the solvent was removed in vacuo. The yellow oil was dissolved in benzene and again concentrated. The residue was dissolved in EA, washed with water, brine, 2 N aq. Na$_2$CO$_3$, and again brine. The org. extract was dried over MgSO$_4$, filtered, concentrated and dried under HV at 85° C. for 30 min to give the expected product as a yellow oil (52.4 g).

$^1$H-NMR (D$_6$-DMSO): δ 3.60 (s, 3H); 3.67 (s, 2H); 7.22 (d, 8.5, 2H); 7.50 (d, J=8.5 Hz, 2H).

B.ii. 2-(4-bromophenyl)-malonic acid dimethyl ester

At 40° C., a solution of intermediate B.i (52 g) in THF (100 mL) was carefully added over a period of 40 min to a suspension of NaH (15.6 g) in dry THF (450 mL). Stirring was continued for 70 min without heating and the temperature dropped to 27° C. The evolution of gas stopped before dimethylcarbonate (76.42 mL) was added dropwise while the temperature of the mixture was maintained at 29-31° C. Stirring was continued for 22 h at rt. The mixture was cooled to −10° C. and then carefully neutralized to pH 6-7 with aq. HCl before bulk of the THF was removed in vacuo. The residue was dissolved in EA (700 mL), washed 3 times with 1 N aq. HCl-solution and once with brine, dried over MgSO$_4$. Most of the EA was evaporated before Hex was added. The product crystallised overnight at 4° C. The crystals were collected, washed with Hex and dried to give the expected product as pale yellow crystals (45.9 g).

$^1$H-NMR (D$_6$-DMSO): δ 3.66 (s, 6H); 5.07 (s, 1H); 7.30-7.34 (m, 2H); 7.55-7.59 (m, 2H),

B.iii. 5-(4-bromophenyl)-pyrimidine-4,6-diol

A solution of intermediate B.ii (11.73 g) in MeOH (100 mL) was added at 0° C. to a solution of sodium (2.83 g) in MeOH (100 mL). The mixture was stirred for 18 h at rt before formamidine hydrochloride (4.10 g) was added. The suspension was stirred at rt for 4 h. The solvent was removed and the residue was suspended in 10% aq. citric acid (100 mL) and stirred for 10 min. The white precipitate was collected, washed with 10% aq. citric acid, water, evaporated three times from cyclohexane and dried under HV at 40° C. to give 5-(4-bromophenyl)-pyrimidine-4,6-diol as a pale beige powder (9.90 g).

$^1$H-NMR (D$_6$-DMSO): δ 7.43-7.48 (m, 2H), 7.50-7.55 (m, 2H), 8.13 (s, 1H), 12.1 (s br., 2H).

LC-MS: t$_R$=0.62 min, [M+H]$^+$=266.89/268.89 (Br-isotopes).

B.iv. 5-(4-bromo-phenyl)-4,6-dichloro-pyrimidine

To a suspension of 5-(4-bromophenyl)-pyrimidine-4,6-diol (9.90 g) in POCl$_3$ (130 mL) was carefully added N,N-dimethylaniline (13.5 mL). The mixture is heated to 130° C. for 2 h. The dark brown solution is concentrated in vacuo and the residue was poured into ice/water. The suspension is diluted with 2 N HCl and water and stirred for 20 min. The precipitate that formed is collected and washed with water. The solid material is dissolved in EA, washed with 1 N aq. HCl and brine. The org. phase is dried over MgSO$_4$ and evaporated. The material is further purified by column chromatography on silica gel eluting with Hex:EA 95:5 to 1:1 followed by crystallisation from Hex/EA at −20° C. to give 4,6-dichloro-5-(4-bromophenyl)-pyrimidine as pale yellow crystals (8.3 g).

$^1$H-NMR (D$_6$-DMSO): δ 7.39-7.44 (m, 2H), 7.72-7.76 (m, 2H), 8.94 (s, 1H).

LC-MS: t$_R$=1.02 min.

Example 1

{5-(4-bromo-phenyl)-6-[2-(5-bromo-pyrimidin-2-yloxy)-ethoxy]-pyrimidin-4-yl}-sulfamide 1.i. Benzyl-sulfamic acid [6-chloro-5-(4-bromophenyl)-pyrimidin-4-yl]-amide A solution of 5-(4-bromophenyl)-4,6-dichloro-pyrimidine (4.00 g, 13.2 mmol) and benzylsulfamide potassium salt (7.38 g, 32.9 mmol) in DMSO (30 mL) was stirred at it for 24 h before being diluted with a 10% aq. citric acid solution (200 mL). The suspension that formed was filtered. The collected solid was washed well with water and dried under HV at 40° C. for 48 h to give the expected product as a white powder (6.15 g).

$^1$H NMR (CDCl$_3$): δ 4.23 (d, J=5.9 Hz, 2H); 5.94 (t br., J=6 Hz, 1H); 7.05 (d, J=8.2 Hz, 2H); 7.20-7.35 (m, 5H); 7.68 (d, J=8.2 Hz, 2H); 8.61 (s, 1H).

LC-MS: t$_R$=1.02 min, [M+H]$^+$=452.95.

1.ii. Benzyl-sulfamic acid [5-(4-bromophenyl)-6-(2-hydroxyethoxy)pyrimidin-4-yl]-amide t-BuOK (18.5 g, 164.5 mmol) was added portionwise to a suspension of intermediate 1.i (7.46 g, 16.4 mmol) in ethylene glycol (50 mL). The mixture became warm and thick and was diluted with DME (75 mL). The mixture was stirred at 95° C. for 24 h before it was cooled to rt, diluted with water (50 mL) and a 10% aq. citric acid solution (250 mL). The milky suspension was extracted with EA (2×300 mL). The combined org. extracts were dried over MgSO$_4$, filtered and the filtrate was concentrated. The remaining crystalline solid was suspended in MeOH, collected, washed well with MeOH and dried under HV to give the expected product as a white crystalline powder (6.49 g).

$^1$H NMR (CDCl$_3$): δ 2.50 (t br., J=6 Hz, 1H); 3.80-3.88 (m, 2H); 4.20 (d, J=5.9 Hz, 2H); 4.46-4.50 (m, 2H); 5.99 (t br., J=6.4 Hz, 1H); 6.85 (s br., 1H); 7.12 (d, J=8.2 Hz, 2H); 7.23-7.34 (m, 5H); 7.64 (d, J=8.2 Hz, 2H); 8.44 (s, 1H).

LC-MS: t$_R$=0.93 min, [M+H]$^+$=479.08.

1.iii Benzyl-sulfamic acid [5-(4-bromophenyl)-6-{2-(5-bromo-pyrimidin-2-yloxy)-ethoxy}-pyrimidin-4-yl]-amide To a solution of intermediate 1.ii (6.49 g, 13.5 mmol) in THF (120 mL) was added carefully NaH (1.77 g, 40.6 mmol, 55% dispersion in mineral oil). The mixture was stirred for 10 min before 2-chloro-5-bromo-pyrimidine (3.93 g, 20.3 mmol) was added. The mixture was diluted with DMF (15 mL) and then stirred at rt for 20 min. The mixture was heated to 60° C. and stirred for 3 h before being again cooled to rt. The reaction was quenched with water and 10% aq. citric acid solution (250 mL) and the mixture was extracted with EA (2×300 mL). The org. extracts were washed with water, combined, dried over MgSO$_4$, filtered and the solvent of the filtrate was evaporated. The crude product was crystallised from MeOH/ether. The crystalline material was collected, washed with additional MeOH/ether and dried under HV to give the expected product as a white powder (6.47 g).

$^1$H NMR (CDCl$_3$): δ 4.20 (d, J=6.4 Hz, 2H); 4.59-4.64 (m, 2H); 4.69-4.74 (m, 2H); 5.98 (t br., J=6.4 Hz, 1H); 6.83 (s br., 1H); 7.06-7.10 (m, 2H); 7.24-7.34 (m, 5H); 7.54-7.58 (m, 2H); 8.44 (s, 1H); 8.50 (s, 2H).

LC-MS: t$_R$=1.06 min, [M+H]$^+$=634.98.

1.iv. {5-(4-bromo-phenyl)-6-[2-(5-bromo-pyrimidin-2-yloxy)-ethoxy]-pyrimidin-4-yl}-sulfamide A solution of borontribromide (25.5 mL, 1 M in DCM) was slowly added to a solution of intermediate 1.iii (6.50 g, 10.2 mmol) in chloroform (250 mL). The mixture became turbid and an oily residue separated. The mixture was stirred at rt. Another portion of BBr$_3$ solution (5 mL) was added after 6, 24, and 33 h. After the last addition of BBr$_3$, the beige suspension was stirred vigorously for additional 2 h before being carefully quenched with MeOH. The mixture became slightly warm and clear. The solution was washed with cold water (0° C., 2×150 mL). The washings were extracted back with DCM. The combined org. extracts were again washed with water, dried over MgSO$_4$, filtered and concentrated. The crude product was purified by CC on silica gel eluting with heptane:EA 1:1 followed by crystallisation from DCM. The purified crystalline product was dried under HIV at 45° C. for 48 h to give the expected product as a white, crystalline powder (1.62 g).

$^1$H NMR (CDCl$_3$): δ 4.60-4.65 (m, 2H), 4.71-4.74 (m, 2H), 5.50 (s br, 2H), 7.10 (s br, 1H), 7.13-7.17 (m, 2H), 7.55-7.59 (m, 2H), 8.49 (s, 2H), 8.50 (s, 1H).

LC-MS: t$_R$=0.93 min, [M+H]$^+$=544.70.

Pharmacological Properties of the Invention Compound

1) Inhibition of Endothelin Binding to Membranes from CHO Cells Carrying Human ET Receptors Experimental Methods:

For competition binding studies, membranes of CHO cells expressing human recombinant ET$_A$ or ET$_B$ receptors were used. Microsomal membranes from recombinant CHO cells were prepared and the binding assay made as previously described (Breu V., et al, *FEBS Lett*. (1993), 334, 210).

The assay is performed in 200 μL 50 mM Tris/HCl buffer, pH 7.4, including 25 mM MnCl$_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After 2 h, the membranes were filtered on filterplates containing GF/C filters (Unifilterplates from Canberra Packard S.A. Zurich, Switzerland). To each well, 50 μL of scintillation cocktail is added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay is run in the presence of 2.5% DMSO which is found not to interfere significantly with the binding. IC$_{50}$ is calculated as the concentration of antagonist inhibiting 50% of the specific binding of ET-1. For reference compounds, the following IC$_{50}$ values were found: ET$_A$ cells: 0.075 nM (n=8) for ET-1 and 118 nM (n=8) for ET-3; ET$_B$ cells: 0.067 nM (n=8) for ET-1 and 0.092 nM (n=3) for ET-3.

Results:

The IC$_{50}$ values obtained for the compound of formula I are given in Table 1 hereafter.

TABLE 1

| Compound structure [remark] | ET$_A$ IC$_{50}$ (nM) | ET$_B$ IC$_{50}$ (nM) |
|---|---|---|
| [compound of formula I] | 3.7 | 1280 |

2) Inhibition of Endothelin-Induced Contractions on Isolated Rat Aortic Rings (ET$_A$ Receptors) and Rat Tracheal Rings (ET$_B$ Receptors)

Experimental Methods:

The functional inhibitory potency of the endothelin antagonists was assessed by their inhibition of the contraction induced by endothelin-1 on rat aortic rings (ET$_A$ receptors) and of the contraction induced by sarafotoxin S6c on rat tracheal rings (ET$_B$ receptors). Adult Wistar rats were anesthetized and exsanguinated. The thoracic aorta or trachea were excised, dissected and cut in 3-5 mm rings. The endothelium/epithelium was removed by gentle rubbing of the intimal surface. Each ring was suspended in a 10 mL isolated organ bath filled with Krebs-Henseleit solution (in mM; NaCl 115, KCl 4.7, MgSO$_4$ 1.2, KH$_2$PO$_4$ 1.5, NaHCO$_3$ 25, CaCl$_2$ 2.5, glucose 10) kept at 37° C. and gassed with 95% O$_2$ and 5% CO$_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the EC$_{50}$ induced by different concentrations of test compound. EC$_{50}$ is the concentration of endothelin needed to get a half-maximal contraction, pA$_2$ is the negative logarithm of the antagonist concentration which induces a two-fold shift in the EC$_{50}$ value.

Results:

The pA$_2$ values obtained for the compound of formula I (n=3) are given in Table 2 hereafter.

TABLE 2

| Compound structure [remark] | pA$_2$ aorta (rat) | pA$_2$ trachea (rat) |
|---|---|---|
| 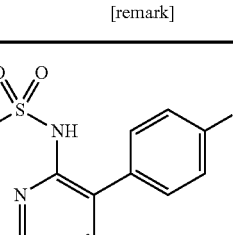 [compound of formula I] | 6.7 ± 0.2 | 5.5 ± 0.3 |

Pharmacokinetics in the Rat After Single-Dose Oral Administration

Experimental Methods:

Animals Used for Carrying Out the Study

Male Wistar rats with a body weight of 200-250 g were used for pharmacokinetic experiments after an acclimatization period of at least 7 days. All animals were housed under conditions in accordance with the NIH guidelines. Two days prior to the experiment, rats were anesthetized with a mixture of ketamin (90 mg/kg) and xylazine 2% (10 mg/kg) i.p. A catheter was implanted under aseptic conditions into the jugular vein to allow for multiple blood sampling. After recovery from general anesthesia, animals were housed individually under standard laboratory conditions in Makrolon type-3 cages with wire mesh tops and standardized softwood bedding. Animals had free access to water and food during the recovery period and the entire duration of the experiment.

Experimental Procedure

Pharmacokinetic experiments were performed in Wistar rats (m=2-3) after jugular vein cannulation to allow for serial blood sampling. Test compounds were administered orally by gavage at doses of 10 mg/kg. Blood was then sampled at pre-defined time points over a period of 24 h and plasma prepared by centrifugation. Drug concentrations in plasma were quantified using liquid chromatography coupled to mass spectrometry (limit of quantification: 4.6 ng/mL). Pharmacokinetic evaluation was performed using non-compartmental analysis.

Results:

The half-life times $t_{1/2}$ and the clearance rates CL measured in the rat for the compound of formula I and for a reference compound of WO 02/053557 can be found in Table 3 hereafter.

TABLE 3

| Compound structure [remark] | $t_{1/2}$ (h) | CL (ml.min$^{-1}$.kg$^{-1}$) |
|---|---|---|
| [compound disclosed in WO 02/053557] | 2.8-4.2 | 5.7-10.0 |
| [compound of formula I] | 8.7 | 1.3 |

Pharmacokinetics in Man After Multiple-Dose Oral Administration

Experimental Methods:

This study was performed as a double-blind, placebo-controlled, randomized, ascending dose Phase I study.

Subjects Enrolled in the Study

Per tested dose level, 8 healthy male subjects were enrolled into the clinical study after having been checked for their eligibility during a screening examination.

Eligible subjects had to meet all of the following inclusion criteria:

Male aged between 20 and 50 years (inclusive);
Healthy on the basis of medical history and the assessments performed at screening;
Body mass index between 18 and 28 kg/m$^2$;
Normal blood pressure (BP) and pulse rate (PR), i.e., SBP: 100-140 mmHg, DBP: 50-90 mmHg and PR: 45-90 bpm after 10 min in the supine position (limits included);
12-lead ECG without clinically relevant abnormalities;
Hematology, biochemistry, and urinalysis test results not deviating from the normal range to a clinically relevant extent;
Negative results from drug screen (cocaine, cannabinoids, opiates, benzodiazepines, barbiturates, tricyclic antidepressants, methadone, and amphetamines);
Ability to communicate with the investigator in the local language, and to understand and comply with the requirements of the study.

Eligible subjects had to meet none of the following exclusion criteria:

Within the 3-year period prior to screening, history or clinical evidence of alcoholism or drug abuse;

Within the 3-year period prior to screening, history or clinical evidence of any disease and/or existence of any surgical or medical condition which might interfere with the absorption, distribution, metabolism or excretion of the study drug (i.e., impaired hepatic or renal function, diabetes mellitus, cardiovascular abnormalities, pancreatic diseases, chronic symptoms of pronounced constipation or diarrhea, or other acute symptoms related to the gastrointestinal tract with only appendectomy or herniotomy allowed);

History of hepatitis B or C and/or positive results from the hepatitis serology which indicate acute or chronic hepatitis B or C (except for vaccinated subjects);

Positive results from the HIV serology;

Smoking;

History of clinically relevant hypersensitivity or serious adverse reactions to any drug;

Participation in another clinical study during the 3-month period prior to the screening examination;

Previous or concomitant treatment with any medication (either prescribed or OTC) from 2 weeks prior to the first drug intake;

Loss of 250 ml or more of blood within 3 months before the study;

Symptoms of a clinically relevant illness in the 4-week period preceding screening (e.g., acute bacterial, viral, or fungal infection).

Concomitant Medications, Dietary Aspects, Alcohol, Smoking, Physical Activities

No concomitant medication was allowed except for the treatment of adverse events.

The subjects fasted from 10 hours prior to 4 hours after drug intake on study days 1 and 10. During the study, the subjects received the following standardized meals:

breakfast on days −1, and 2 to 11 (no breakfast on days 1 and 10);

lunch on days −1, 1 and 10 around noon or approximately 4 hours after drug intake;

snack on days −1, 1, and 10 approximately 8 hours after drug administration; and dinner on days −1, 1, and 10 approximately around 19.00 h or approximately 11 hours after drug administration.

The subjects in the different dose groups received the same meals on the respective study days. The meals on days 1 and 10 were the same. The intake of water was ad libitum.

From screening until the end-of-study examination, the subjects refrained from strong physical exercise and strenuous sports activities (endurance sports) and did not consume any alcohol-containing beverages, grapefruit or grapefruit juice. Drinking of xanthine-containing beverages was not permitted in the clinic.

Experimental Procedure

Propylsulfamic acid [5(4 bromo-phenyl)-6-[2-(5-bromo-pyrimidin-2-yloxy)-ethoxy]-pyrimidin-4-yl]-amide (see WO 02/053557 or WO 2007/031933; hereafter named the "Reference Compound") was available as a free base for clinical trial use in hard gelatin capsules for oral administration, formulated at strengths of 1 and 10 mg. Matching placebo capsules contained the same excipients without the Reference Compound.

The Reference Compound was administered as ascending multiple doses of 1, 3, 10 and 30 mg (respectively in the form of 1 capsule of 1 mg, 3 capsules of 1 mg, 1 capsule of 10 mg and 3 capsules of 10 mg). Subjects were treated for 10 days. The assignment of number and code for the subject identification was based on the obligation for anonymity. Only their subject number and date of birth did identify subjects.

This study was performed in a double-blind fashion. Per dose level 6 subjects were randomized to treatment with Reference Compound and 2 subject to treatment with placebo.

Medication was given with 150 ml of water in the morning to subjects in the standing position, after they had fasted for at least 10 hours on days 1 and 10. On other study days, study drug administration was done 30 min prior to the intake of breakfast. For each subject, the interval between each drug intake was 24±0.5 hours but drug intake took always place between 7.00 and 9.00 h.

All drug administrations were done under direct medical supervision. A mouth check was done immediately after each drug administration. The measurement of plasma levels of the Reference Compound and/or its metabolite, i.e. the compound of formula I, during the analytical phase served as a further check of compliance.

The concentration of the Reference Compound and its metabolite, i.e. the compound of formula I, in plasma and urine were determined using LC-MS. The limit of quantification was estimated to be 1 ng/ml for both analytes.

Results:

The apparent elimination half-lives ($t_{1/2}$) measured in man at day 10 of the study for the compound of formula I and for the Reference Compound with respect to each of the different doses administered daily (1, 3, 10 and 30 mg respectively) can be found in Table 4 hereafter (the data are geometric means).

TABLE 4

| | $t_{1/2}$ (h) | | | |
| --- | --- | --- | --- | --- |
| Compound | 1 mg dose | 3 mg dose | 10 mg dose | 30 mg dose |
| Reference Compound | 15.2 | 18.5 | 13.7 | 14.3 |
| Compound of formula I | 46.6 | 55.8 | 43.0 | 47.0 |

Summary of the Pharmacological Properties of the Invention Compound

As can be seen, the compound of formula I is an endothelin receptor antagonist (see "Inhibition of endothelin binding to membranes from CHO cells carrying human ET receptors", Table 1 and "Inhibition of endothelin-induced contractions on isolated rat aortic rings ($ET_A$ receptors) and rat tracheal rings ($ET_B$ receptors)", Table 2) that has a much higher half-life (in rats and in humans) and a much lower clearance (in rats) than the reference compound of WO 02/053557 (see "Pharmacokinetics in the rat after single-dose oral administration", Table 3 and "Pharmacokinetics in man after multiple-dose oral administration", Table 4).

The invention claimed is:
1. The compound having the formula I

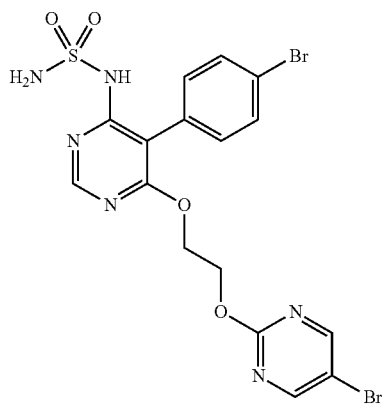

or a salt thereof.

2. A compound of formula I as defined in claim 1, or a pharmaceutically acceptable salt thereof.

3. A pharmaceutical composition containing, as active principle, the compound of formula I as defined in claim 1 or a pharmaceutically acceptable salt thereof, and at least one therapeutically inert excipient.

4. A method for the treatment of hypertension comprising administering to a patient in need thereof, a pharmaceutically effective amount of a compound according to claim 1, or a pharmaceutically acceptable salt form.

5. A method for the treatment of pulmonary hypertension comprising administering to a patient in need thereof, a pharmaceutically effective amount of a compound according to claim 1, or a pharmaceutically acceptable salt form.

6. A method for the treatment of pulmonary arterial hypertension comprising administering to a patient in need thereof, a pharmaceutically effective amount of a compound according to claim 1, or a pharmaceutically acceptable salt form.

7. A process for the preparation of the compound of formula I according to claim 1, which process comprises the following steps:
a) reacting a compound of formula I-2$_B$

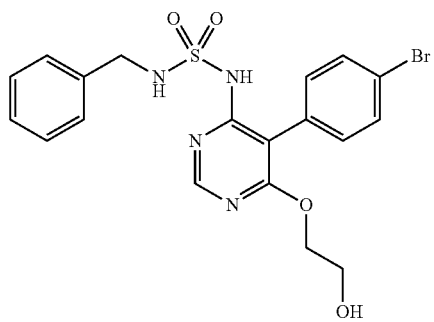

with a compound of formula I-3

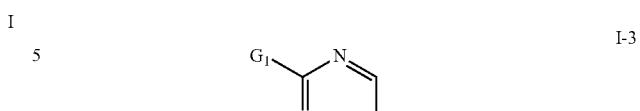

wherein $G_1$ represents a chlorine or bromine atom or a methylsulfonyl or ethylsulfonyl group, in the presence of a strong base; and b) cleaving the benzyl group of the compound of formula I-1$_B$ obtained in step a)

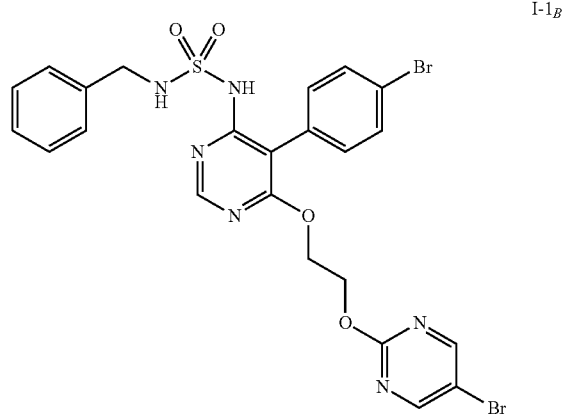

using, $BCl_3$ or $BBr_3$.

8. The process of claim 7, which comprises the additional step of reacting a compound of formula I-4

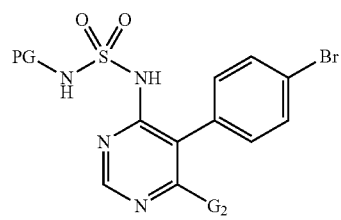

wherein PG represents benzyl and $G_2$ represents a halogen atom with ethylene glycol in the presence of a base to obtain the compound of formula I-2$_B$.

* * * * *